United States Patent [19]

Whitaker, Sr.

[11] Patent Number: 5,051,305
[45] Date of Patent: Sep. 24, 1991

[54] STABILIZED PERFUME-CONTAINING MICROCAPSULES AND METHOD OF PREPARING THE SAME

[75] Inventor: Douglas M. Whitaker, Sr., Chattanooga, Tenn.

[73] Assignee: Arcade, Inc., Chattanooga, Tenn.

[21] Appl. No.: 292,495

[22] Filed: Dec. 30, 1988

[51] Int. Cl.$^5$ .................. B01J 13/08; B01J 13/20; A61K 7/46

[52] U.S. Cl. .................. 428/402.2; 264/4.1; 264/4.3; 512/2; 512/4; 428/321.5; 428/402.24; 424/490; 424/495

[58] Field of Search .................. 428/402.2, 402.24; 512/2, 4; 424/492, 488, 490, 495; 264/4.1, 4.3

[56] References Cited

U.S. PATENT DOCUMENTS

| | | | |
|---|---|---|---|
| 3,155,590 | 11/1964 | Miller et al. | 167/83 |
| 3,205,175 | 9/1965 | Maierson | 428/402.2 X |
| 3,247,066 | 4/1966 | Milosovich, Jr. | 424/490 X |
| 3,516,941 | 7/1966 | Matson | 252/316 |
| 3,576,760 | 4/1971 | Gould et al. | 424/487 X |
| 3,857,964 | 12/1974 | Yolles | 426/3 |
| 3,909,444 | 9/1975 | Anderson et al. | 424/488 X |
| 4,123,381 | 10/1978 | Morishita et al. | 424/488 X |
| 4,209,417 | 6/1980 | Whyte | 512/4 X |
| 4,277,364 | 7/1981 | Shasha et al. | 252/316 |
| 4,339,356 | 7/1982 | Whyte | 512/4 X |
| 4,386,106 | 5/1983 | Merritt et al. | 264/4.3 X |
| 4,528,125 | 7/1985 | Alderman et al. | 512/4 |
| 4,652,441 | 3/1987 | Okada et al. | 428/402.2 X |
| 4,708,834 | 11/1987 | Cohen et al. | 264/4.3 |
| 4,976,961 | 12/1990 | Norbury et al. | 428/402.21 |

Primary Examiner—Richard D. Lovering
Assistant Examiner—John M. Covert
Attorney, Agent, or Firm—Phillips & Beumer

[57] ABSTRACT

Rupturable microcapsules made up of very small droplets or globules of perfume oil encapsulated with an inert polymeric wall are stabilized by providing ethyl cellulose in the perfume oil. This measure prevents escape of higher volatility components of the oil, which would otherwise occur during the preparation process. The stabilized microcapsules may be prepared by a liquid bath encapsulation method wherein ethyl cellulose is first dissolved in the starting oil, and the resulting solution is emulsified by mixing with a gelatin solution in water. The emulsion is then combined with a coacervant and cross-linking agent. Upon cooling the system, a gelatin-based wall coating is deposited around the emulsified particles. Fragrance characteristics of the starting perfume are preserved by this means.

12 Claims, No Drawings

STABILIZED PERFUME-CONTAINING MICROCAPSULES AND METHOD OF PREPARING THE SAME

FIELD OF THE INVENTION

This invention relates to perfume-containing microcapsules and to methods for preparing them.

BACKGROUND OF THE INVENTION

Microcapsules comprising droplets of fill material such as a perfume oil encased by a shell of inert, rupturable material are well known in the prior art. They are commonly used by being applied to advertising material or incorporated in an adhesive layer between sheets of paper intended for being torn apart. Upon being scratched or or upon tearing of such adhesive layer, the microcapsules are ruptured, releasing perfume fragrance. Typical microcapsules for such applications have a particle size ranging upward from a few microns, and their shell is made of polymeric material such as a urea-formaldehyde condensation product.

A continuing problem has existed in the use of perfume-containing microcapsules for advertising sampler applications. Most fragrance compositions contain many low-molecular-weight compounds, which by their nature have a tendency to be extremely volatile. In currently used processes, perfume droplets, during emulsification and prior to being encapsulated, are exposed to necessary process temperatures high enough to vaporize highly volatile components, leaving behind an incomplete version of the fragrance. One approach to solving this problem has been to provide a starting perfume that has been modified by overloading it with the lower-molecular-weight, more volatile compounds to compensate for their loss in processing. This approach has often required several attempts to reach the desired result and does not carry any certainty of success, but rather is in the nature of a "hit or miss" procedure. Thus, a need exists for a means of entrapping the perfume within the perfume oil droplets and preventing volatilization during processing. The microcapsules should also exhibit stability after preparation to provide necessary shelf-life up to the time of their being ruptured by a customer.

Numerous prior art patents disclose perfume-containing microcapsules and processes for preparing them. Encapsulation processes of various types are discussed in U.S. Pat. No. 4,277,364 and other references cited therein. U.S. Pat. No. 3,516,941 discloses that organic liquid drops being encapsuled by polymerization of urea-formaldehyde shells around the droplets may carry sealing agents, in particular, ethyl cellulose in xylene droplets, the sealing agent forming a liner separating the droplet from the shell wall. No mention is made as to whether such measure would be effective for entrapping perfume oils so as to avoid differential loss of more volatile components of the oil or of applying it to gelatin-walled microcapsules.

SUMMARY OF THE INVENTION

This invention is directed to rupturable microcapsules having droplets or globules of ethyl-cellulose-containing perfume oil enclosed by a wall of inert polymeric material, the perfume oil including components of varying volatility. Ethyl cellulose when dissolved in perfume oil provides a matrix in which the oil is entrapped, thus inhibiting release of highly volatile fragrances during processing. The resulting stabilized droplets maintain their integrity, and any need for overloading the starting material with more volatile components is avoided. Microcapsules embodying the invention may be prepared by a liquid bath encapsulation method wherein ethyl cellulose is first dissolved in the starting oil, and the resulting solution is emulsified by mixing with a gelatin solution in water. The emulsion is then combined with a coacervant such as an aqueous solution of gum arabic and an aldehyde cross-linking agent. Upon cooling the emulsion, a gelatin-based wall is deposited around the emulsified particles, and the resulting microcapsules are recovered. The ethyl-cellulose-containing oil droplets may also be encapsulated by other methods. Microcapsules ideally suited for advertising sampler applications are readily obtained by this means.

It is, therefore, an object of this invention to provide stabilized perfume-containing microcapsules.

Another object is to provide perfume-containing microcapsules having substantially the same fragrance content as the perfume used for starting material.

Yet another object is to provide a method for preventing loss of highly volatile perfume components during preparation of microcapsules containing droplets of perfume.

Other objects and advantages of the invention will be apparent from the following detailed description and claims appended hereto.

DESCRIPTION OF THE PREFERRED EMBODIMENT

The starting perfume oil may comprise natural or synthetic fragrances or essential oils. As discussed above, such materials typically include a variety of components differing from one another in their molecular weight and volatility. In order to stabilize the oil for processing into microcapsules, ethyl cellulose is added to the oil, preferably at a proportion of 5 weight percent of the weight of the oil, although other amounts may be used. Ethyl cellulose is normally identified by its viscosity, with a higher viscosity material having a higher molecular weight. Best results are obtained with material having a viscosity of 6 to 8 centipoise, such product being available from Dow Chemical Company under the designation Etholcel-7 TM. Other suitable products available from the same source and having higher viscosities are Ethocel-10 TM and Ethocel-20 TM. The ethyl cellulose readily dissolves in perfume oils, creating an environment that fragrances have an affinity for.

An emulsion of ethyl-cellulose-containing perfume oil droplets in an aqueous system is prepared by combining the oil with gelatin and water and thoroughly agitating the mixture. For Ethocel-7 TM ethyl cellulose material at the concentration given above, 120 ml of fragrance oil may be combined with 100 grams of water and 90 grams of an aqueous gelatin solution. Emulsification may be carried out in a conventional blender, with droplets of smaller particle sizes being obtainable by longer periods of agitation. A temperature of 35° to 40° C. and a pH of 4.75 give best results.

The resulting emulsion is combined with an agent that produces complex coacervation in the system, inducing phase separation between two separate and distinct liquid phases. Both phases contain the same components with one phase (the coacervate) having a much greater concentration of colloid than the other. Encapsulation occurs when small droplets of oil are present in the collodial suspension and the system is cooled, the coacervate being deposited around individual droplets. Gum arabic and sodium polyphosphates may be used for this purpose, with gum arabic in the form of an 11 percent aqueous solution being preferred. For an emulsion mixture as described above, 90 grams of such solution may be used. Dilution of the system such as by addition of 200 grams of water may be carried out at this point to provide more effective process.

A cross-linking agent may be used to assist in initial solidification of deposited gelatin capsule walls. Aldehydes, and in particular, glutaraldehyde, may be used for this purpose. For the amounts of system components given above, 5 ml of a 25% aqueous solution of glutaraldehyde gives best results.

Cooling of the system down to a temperature below 10° C. is required for deposition of capsule wall material on the droplets. This may be carried out by use of an ice bath, the system being brought down to that temperature held there for a period, such as one hour. Upon completion of encapsulation, the resulting microcapsules may be recovered by filtration.

Microcapsules prepared as described above, in addition to providing, upon being ruptured, a fragrance that accurately corresponds to the fragrance of the starting perfume, exhibit a significant increase in shelf-life stability when compared to oils processed under the same conditions but without incorporating ethyl cellulose in the oil.

The invention is further illustrated by the following example.

EXAMPLE

Single oil drop microcapsules having an average diameter of about 25–50 microns are prepared by emulsifying together at 35° to 40° C. with agitation in a Waring blender 90 grams of an 11 percent aqueous dynagel gelatin solution at a pH of about 4.75, 100 grams of water, and 120 ml of fragrance oil loaded with 5 percent Ethocel-7 TM. This emulsion is added to 90 grams of an 11 percent aqueous gum arabic solution at a pH of about 4.75 and 100 grams of water. Two hundred grams of water is added as a final dilution. The resulting system is cooled slowly to about 26° C. and then chilled in an ice bath to about 10° C. and held below 10° C. for one hour. Five ml of a 25% aqueous solution of glutaraldehyde is added to assist in the initial solidification of the resulting capsule walls. The encapsuled fragrance oil obtained amounts to about 20 percent by weight of the total resultant dispersion. The capsules are then filtered and water is added back to the capsules so that the final viscosity of the slurry is 35 seconds on a Zahn #2 cup. In the final slurry, the encapsulated fragrance oil amounts to about 26 percent by weight of the total dispersion.

Additional preparations were carried out by the above procedure except that sodium polyphosphate was used instead of gum arabic, and ethyl cellulose of varying viscosities was used instead of Ethocel-7 TM. Stability tests were conducted wherein the microcapsules were exposed for prolonged periods to a sequence of severe environments as follows: 110° F. for 30 days; 90% relative humidity at 90° F. for 30 days; 40° F. for 30 days; fluctuating every 48 hours from 110° F. to 40° F. for a period of 30 days; alternating freezing and thawing by holding below 32° F. for 24 hours, followed by 24 hours at room temperature for a period of five days. After completion of this sequence, the microcapsules were evaluated for olfactory integrity. Substantially improved results were obtained for ethyl-cellulose containing microcapsules, as compared to those not including this component. Rendition tests wherein the fragrance delivered upon rupture is compared with the starting oil fragrance showed a high degree of improvement.

Although the invention is described above in terms of using a gelatin encapsulant and process, other encapsulant systems such as urea-formaldehyde may also be modified to incorporate ethyl cellulose or a similar droplet-stabilizing additive in the perfume being encapsulated. In addition to ethyl cellulose, other additives which may be used to entrap perfume fragrances include B-cyclodextrin, polyplasdone, Kelcolloid, polyethyleneimine, beeswax, acrylamide, and N-tertbutyl acrylamide.

The invention is not to be understood as limited to the above illustrative example, but is limited only as indicated by the following claims.

I claim:

1. Perfume-containing microcapsules comprising a central core of a droplet or globule of perfume oil including fragrance components of substantially varying volatilities and containing ethyl cellulose in an amount effective to provide a matrix therein, said droplets or globules being encased by an inert polymeric wall material comprising gelatin and a phase-separation-inducing coacervation agent reaction product.

2. Microcapsules as defined in claim 1 wherein said agent is selected from the group consisting of gum arabic and polyphosphates.

3. Microcapsules as defined in claim 2 wherein said agent is gum arabic.

4. Microcapsules as defined in claim 3 including an aldehyde cross-linking agent reaction product contained in said wall material.

5. Microcapsules as defined in claim 4 wherein said cross-linking agent is glutaraldehyde.

6. Microcapsules as defined in claim 1 wherein the amount of ethyl cellulose therein is five weight percent of the perfume oil.

7. Microcapsules as defined in claim 6 wherein said ethyl cellulose has a viscosity of six to eight centipoise.

8. A process for preparing microcapsules containing a perfume oil that includes components of varying volatility which comprises:
   combining said oil with ethyl cellulose in an amount of five weight percent of said oil;
   emulsifying said oil in an aqueous system including gelatin at a temperature of 35° to 40° C., whereby droplets of oil containing ethyl cellulose are obtained;
   combining the emulsion with a coacervation agent and a cross-linking agent; and
   cooling the resulting mixture to a temperature below 10° C. and maintaining such temperature until a gelatin-based wall is deposited around said microcapsules.

9. The process as defined in claim 8 wherein said coacervation agent is gum arabic and said cross-linking agent is glutaraldehyde.

10. In a process for preparing perfume-containing microcapsules for perfume that includes fragrance components of substantially varying volatilities which comprises forming an aqueous emulsion of droplets of said perfume oil and gelatin, combining said emulsion with a coacervation agent and a cross-linking agent, and cooling the resulting system, whereby gelatin is deposited as a wall around said droplets, the improvement comprising:

providing ethyl cellulose in said perfume oil in an amount sufficient to provide a matrix in said microcapsules prior to droplet formation, whereby loss of more volatile components of said oil during said process is minimized.

11. The improvement as defined in claim 10 wherein said ethyl cellulose is provided in said oil in an amount of 5 percent of the weight of the oil.

12. The improvement as defined in claim 11 wherein said ethyl cellulose has a viscosity of 6 to 8 centipoise.

* * * * *